United States Patent [19]

Miyata et al.

[11] 4,215,200

[45] Jul. 29, 1980

[54] CHEMICALLY AND ENZYMATICALLY MODIFIED COLLAGEN HEMOSTATIC AGENT

[75] Inventors: Teruo Miyata, Tokyo, Japan; Kurt H. Stenzel; Albert L. Rubin, Englewood, both of N.J.

[73] Assignee: Cornell Research Foundation, Inc., Ithaca, N.Y.

[21] Appl. No.: 948,003

[22] Filed: Oct. 2, 1978

Related U.S. Application Data

[63] Continuation-in-part of Ser. No. 916,885, Jun. 19, 1978, abandoned, which is a continuation of Ser. No. 782,062, Mar. 28, 1977, abandoned.

[51] Int. Cl.$^2$ .......................... C07G 7/00; C08L 89/06
[52] U.S. Cl. ..................................... 435/273; 128/156; 128/296; 128/334 R; 128/335.5; 128/325; 128/DIG. 8; 106/155; 106/161; 260/123.7; 424/27; 424/28
[58] Field of Search .................... 195/6; 260/123.7; 435/273; 128/DIG. 8; 106/161, 155

[56] References Cited

U.S. PATENT DOCUMENTS

| | | | |
|---|---|---|---|
| 2,973,302 | 2/1961 | Bloch | 195/6 |
| 3,034,852 | 5/1962 | Nishihara | 260/123.7 X |
| 3,071,477 | 1/1963 | Klevens | 195/6 X |
| 3,114,593 | 12/1963 | Griset et al. | 264/103 X |
| 3,157,524 | 11/1964 | Artandi | 260/123.7 X |
| 3,314,861 | 4/1967 | Fujii | 195/6 |
| 3,393,080 | 7/1968 | Erdi et al. | 260/123.7 X |
| 3,632,361 | 1/1972 | Battista | 260/123.7 X |
| 3,637,642 | 1/1972 | Fujii | 260/123.7 X |
| 3,649,347 | 3/1972 | Battista | 260/123.7 X |
| 3,898,129 | 8/1975 | Fujimoto et al. | 195/6 X |
| 4,066,083 | 1/1978 | Ries | 195/6 X |
| 4,140,537 | 2/1979 | Luck et al. | 260/123.7 |

OTHER PUBLICATIONS

Journal of Amer. Chem. Soc., vol. 74, 1952, pp. 4608–4611, Gustavson.
Chem. Abstracts, vol. 47, 1953, 901h–902a–c, Lennox et al.
Chem. Abstracts, vol. 47, 1953, 11787g–i, 11788d–i, 11789a, Cassel et al., Wiederman et al., Danby et al.
Chem. Abstracts, vol. 82, 1975, 113208k, Kipnis et al.
Trans. Amer. Soc. Artif. Int. Organs, Apr., 1976, Miyata et al., vol. XXII.
Chemical Reactions of Polymers, Fettes, 1965, pp. 384–386, 389–392.
Ann. Rev. of Biophysics & Bioengineering, vol. 3, 1974, pp. 231–253, Stenzel et al.
J. Clin. Inv., vol. 54, pp. 1480–1487, Dec., 1974, Brass et al.

*Primary Examiner*—Howard E. Schain
*Attorney, Agent, or Firm*—Edward J. Mahler

[57] ABSTRACT

Polymers of quaternary-structured collagen of minimum length, diameter and periodicity, and containing a relatively high positive electrostatic charge are claimed as hemostatic agents. Specific examples are guanidnated polymers of the type described, esterified polymers, and esterified-guanidinated polymers.

9 Claims, No Drawings

CHEMICALLY AND ENZYMATICALLY MODIFIED COLLAGEN HEMOSTATIC AGENT

The U.S. Government has rights in this invention pursuant to Grant ROI-EYO1502 awarded by the Department of Health, Education and Welfare.

This application is a C.I.P. of Ser. No. 916,885 filed June 19, 1978, which is a continuation of Ser. No. 782,062 filed Mar. 28, 1977, both now abandoned.

This invention relates to the production of chemically modified polymeric collagen hemostatic agents. Specifically, the invention is concerned with a power or gel form of specific polymeric collagen in regularly staggered quarternary structure, further modified to contain a high positive electrostatic charge at physiologic pH or high isoelectric point. More particularly, the invention is concerned with a powder or gel form of such polymeric collagen which has been guanidinated, esterified, and/or esterified-guanidinated.

Platelets play important roles in the initial stages of hemostasis. Platelets adhere to exposed subendthelial connective tissues; additional platelets adhere to the layer of adherent platelets and form a platelet plug to be an effective barrier to further bleeding. The adherent platelets release clot-promoting factors and accelerate blood coagulation.

Native, unmodified collagen contains about 40 lysyl groups, 50 arginyl groups and 120 carboxyl groups per 1000 amino acid residues. Upon dissociation the carboxyl groups are negatively charged, while the lysyl and arginyl groups are positively charged.

It has been found that the guanidino groups of collagen play an important role in platelet-collagen interaction and that destruction of the guanidino groups on native type collagen fibrils (e.g. by reaction with hypobromite) abolishes platelet aggregating activity. Therefore, the introduction of additional guanidino groups into the molecule by guanidination of the lysyl groups greatly increases the opportunity for platelet aggregation, since the guanidinated surfaces being positively charged become attracted to the platelets which are negatively charged. Guanidination of the lysyl residue converts its $NH_2$ group to a homoarginyl residue which is similar to the arginyl residue in that both contain the guanidino group. The homoarginyl residue contains one additional carbon in the chain.

Collagen is a major component of connective tissue and it is well-known that platelets interact with collagen fiber by adhesion and aggregation. In other words, collagen is one of the important physiologic substances for the initiation of hemostasis.

Microcrystalline collagen (MCC) as a hemostat, has been described and its effects reported by recent investigators. For example, the use of MCC in the healing of bleeding bone has been reported as has the comparative effectiveness of MCC versus other agents such as purified gelatine solution and cellulose fiber. The present invention involves an improvement over simple microcrystalline collagen.

We have recently found that: (1) neither monomeric collagen nor esterified monomeric collagen is responsible for platelet aggregation; but that polymeric forms of collagen with regularly staggered quaternary structures are required to cause platelet aggregation; (2) critical minimum size of the collagen polymeric particles required to induce platelet aggregation is 7,000–10,000 A° in length; 20–40 A° in diameter, and at least 670–700 A° periodicity; (3) the arginyl residues of collagen are directly involved in collagen-platelet interaction; (4) platelet and fibrin depositions on guanidinated, methylated or methylated-guanidinated collagen surface were strongly enhanced when unmodified whole blood was exposed to such collagen surfaces. These findings led to the conclusion that an effective collagen hemostatic agent should be an esterified, guanidinated, or esterified-guanidinated collagen polymeric particle with regularly staggered quaternary structure. The term quaternary structure refers to the association of tropocollagen into polymers in which the monomers are structured parallel to each other but staggered by approximately one quarter of their length. We have prepared a powder form and a gel form of collagen hemostatic agents from methylated, guanidinated and methylated-guanidinated regularly staggered quaternary polymer collagens and compared their efficacies as a hemostatic agent with commercially available hemostatic agents and found that the new collagen hemostatic agents were more effective.

The above dimensions are the critical minima for the induction and maintenance of platelet aggregation. There appears to be no maximum except for the practicality of the handling of large size particles. The length of the polymer could be as high as 5 to 10 times the minimum and similarly, the diameter could be 3 to 5 times the minimum size. However, when making a gel as opposed to a powder, a lesser molecule weight and diameter are preferred. The degree of polymerization of tropocollagen is controlled chiefly by controlling the pH of the dialysis solution, e.g., the more basic the solution, the greater the degree of polymerization. Thus, it should be noted, in preparing the gel-type polymer, the dialysis solution was maintained on the more acid side.

The hemostatic effect is the result of enhancing the interaction between platelets and arginyl residues of modified collagen which is brought about indirectly by increasing the net positive charge of collagen or, directly, by increasing the guanidino groups, or by a combination of the two. The increased net positive electrostatic charge is brought about mainly by converting the carboxyl group of the tropocollagen polymer to an ester by reaction with alcohol or other esterforming compound. The increase of guanidino groups is accomplished by reacting the $NH_2$ group of the lysyl residues with chemical substances capable of converting amino to guanidino groups.

When speaking of high electrostatic charge or high isoelectric point it is meant that the chemically modified collagen polymer has, (at physiologic pH, i.e. about 7.4) a higher positive charge or higher isoelectric point than the unmodified collagen. For example, non-modified polymeric collagen has an isoelectric point (pI) of 9.0, but when methylated it has a pI of 10.5 and when methylated and guanidinated its pI exceeds 12.0. During esterification about 85% of the carboxyl groups of the molecule become methylated, and about 50% of the lysyl groups become converted to guanidino groups during the guanidination reaction.

The collagen used in this experiment was enzyme solubilized collagen from calf skin. Bovine skins including steer, cow bull hides and pig skin can also be used as a collagen source. Proteolytic enzymes such as pepsin, pronase, etc. (other than collagenase), digest telopeptides of collagen molecules (terminal parts of molecule) and solubilize insoluble collagen into telopeptide-poor monomeric collagen. Telopeptide-poor collagen is useful as a material of hemostatic agents because its antigenicity is very weak. Regularly staggered polymeric forms are obtained from purified monomeric telopeptide-poor collagen. Native type fibril with 670 A° periodicity is obtained by dialysis of acidic telopeptide-poor collagen against 0.02 M $Na_2HPO_4$ or by adjustment of the pH of telopeptide-poor collagen to 7–8. The powder hemostatic agent is prepared from native type fibril. A polymeric collagen particle big enough to cause platelet aggregation is made by dialysis of telopeptide-poor collagen against a dilute buffer of pH 4.8–5.2. The gel form of hemostatic agent is prepared from the polymeric collagen particle. The quaternary structures of both collagens prepared by these methods are stabilized (cross-linked and/or tanned) by UV-irradiation or aldehyde treatment (formaldehyde, glutaraldehyde) then the guanidination, methylation and methylation-guanidination are carried out. When preparing a hemostat of the gel type, the cross-linking is preferably carried out by UV irradiation rather than aldehyde treatment in order to avoid incorporation of aldehyde residues which are more difficult to remove from the gel type product. Chemically modified native type fibril is dried and pulverized in a Wiley Mill to obtain 100 mesh powder. The chemically modified polymeric collagen particle is redispersed in water of pH 4.8–5.2 to obtain the gel form of the hemostatic agent.

The hemostatic agent of this invention is particularly applicable to the control of bleeding from surfaces, especially large surfaces, rather than control of blood flow from large vessels. For example, the hemostatic agent is useful on (a) cut or severed bone, (b) a severed organ, e.g. spleen, liver or kidney which has been cut surgically or traumatically, (c) the central nervous system where small blood vessels predominate, (d) prosthetic surgery, (e) oozing surfaces resulting from the surgical removal of necrotic tissue, (f) cosmetic surgery and (g) any surfaces with oozing of blood from one or more small sources, e.g. facial cuts.

The hemostatic agent may be applied in a variety of forms, e.g. as a powder directly to the surface; as a styptic in pencil form; as a gel, a sponge or in fabric form. The amount of agent employed varies with the extent of the bleeding surface and severity of the blood flow. Sufficient agent is applied to effect the desired control.

The present invention is disclosed in detail by the following examples:

EXAMPLE 1:

Fresh calf skin of about 5 kg was dehaired, cleaned by shaving and ground in a meat grinder. The skin was solubilized in 10 liters of water (pH 2.5, HCl) by 1 gram of pepsin (approximate ratio of enzyme to collagen is 1/400) at 20° for five days by intermittent stirring. Viscous solubilized collagen was filtered through cheesecloth and its pH adjusted to 10 by NaOH and allowed to stand for 24 hours at 4° C. to inactivate pepsin. The pH of collagen was adjusted to 7 to 8 and collagen precipitate was collected by centrifugation and washed with water three times. This enzyme solubilized collagen (telopeptide-poor collagen) was then lyophilized.

100 grams of lyophilized collagen was dissolved in 5 liters of pH 2.0 water (HCl) by stirring and dialyzed against 25 liters of 0.02 M $Na_2HPO_4$. The dialysate was changed twice. White native type fibril (670A° periodic form) was precipitated, collected by centrifugation and washed twice with water. The fibril was stabilized in 2 liters of 0.1% gluteraldehyde of pH 7.2 phosphate buffer (10.35 grams $KH_2PO_4 \cdot 7H_2O$ in 10 liters $H_2O$) for 30 minutes, washed with water three times and lyophilized. Lyophilized stabilized collagen was methylated in 2 liters of dehydrated methanol containing 0.1 M HCl for 7 days at room temperature in a tightly sealed vessel. Dehydration of methanol containing HCl prior to addition of collagen was carried out by intermittent stirring with excess anhydrous sodium sulfate. After methylation, the collagen product was dried in a vacuum and pulverized in a Wiley Mill with 100 mesh sieve. Powdered collagen hemostatic agent prepared by this method was more effective than commercially available ones, e.g. Avitene (microcrystalline collagen) and revealed no foreign body reaction and only minimal inflammatory reaction in a dog.

EXAMPLE 2:

According to the procedure of Example 1, native type fibril (670 A° periodic form) was pepared by dialysis against 0.02 M $Na_2HPO_4$. After being taken from dialysis tubing, collagen fibril was homogenized in a Waring blender to make a milky suspension. The homogenate was stabilized by irradiation under ultraviolet light (UV) in a quartz flask of 10 liters in the presence of nitrogen. The UV irradiation chamber was equipped with four 15 watt germicidal lamps radiating primarily at 2537 A°. The quartz flask containing collagen homogenate was placed on an ice bucket in the center of the chamber. Irradiation was carried out for 2 hours. Irradiated collagen was collected by centrifugation washed with water three times and lyophilized.

Methylation of UV-irradiated collagen was carried out by the same procedure as that of Example 1. Dried methylated collagen was pulverized in a Wiley mill with 100 mesh sieve. Powdered collagen hemostatic agent prepared by this method is more effective than commercially available ones and revealed no foreign body reaction and but minimal inflammatory reaction in a dog.

EXAMPLE 3:

Native type collagen fibril was prepared by dialysis of enzyme solubilized collagen against 0.02 M $Na_2HPO_4$ and washed with waer twice according to the method of Example 1. The collagen fibril was guanidinated by the following procedure. One hundred grams (100 g) of collagen (dry weight) was suspended in 1 liter water and the pH adjusted to 9.5 by adding NaOH. 80 grams of 1-Guanyl-3,5 dimethylpyrazole nitrate were dissolved in 1 liter of water and pH was adjusted to 9.5. Collagen suspension and the reagent solution were mixed together and allowed to stand for 7 days at 40° C. at pH 9.5 with intermittent stirring. The quaternary structure of native type collagen fibril was stable in this reaction condition. After guanidination the collagen was collected by centrifugation and washed with water three times. Guanidinated collagen was then stabilized with 2 liters of 0.1% glutaraldehyde of pH 7.2 phosphate buffer (See Example 1) for 30 minutes, washed with water twice and lyophilized. The lyophilized product was pulverized in a Wiley Mill with a 100 mesh sieve.

Powdered collagen hemostatic agent prepared by this method is more effective than commercially available ones including microcrystalline collagen (Avitene) and revealed no foreign body reaction and but minimal inflammatory reaction in a dog.

EXAMPLE 4:

After guanidinated collagen was prepared according to the procedure in Example 3, the collagen was then stabilized by UV irradiation as described in the procedure of Example 2. Dried guanidinated collagen was pulverized in a Wiley Mill with 100 mesh sieve.

Powdered collagen hemostatic agent prepared by this method is more effective than commercially available ones and reveals no foreign body reaction, minimal inflammatory reaction in a dog.

EXAMPLE 5:

The guanidinated-glutaraldehyde-fixed collagen was prepared as described in the procedure of Example 3. This collagen was then methylated by the same method as that of Example 1 and finally pulverized by a Wiley Mill with a 100 mesh sieve.

This guanidinated-methylated collagen hemostatic agent is more effective than commercial ones and reveals no foreign body reaction, minimal inflammatory reaction in a dog.

EXAMPLE 6:

Methylated UV-irradiated collagen was prepared by the method of Example 2. One hundred grams of this collagen was further guanidinated by the method of Example 3. After guanidination, collagen was washed in water three times and dried in a vacuum dryer. The product was pulverized in a Wiley Mill with 100 mesh sieve.

Powdered methylated-guanidinated collagen hemostatic agent prepared by this method is more effective than commercial ones and revealed no foreign body reaction and only minimal inflammatory reaction in a dog.

EXAMPLE 7:

Enzyme solubilized collagen was prepared by the method of Example 1. One hundred grams of this collagen was dissolved in 5 liters of pH 2.0 water (HCl) by stirring and dialyzed against 25 liters of 0.001 M acetate buffer, pH 5.0 at 4° C. Dialysate was changed three times. Under these conditions the collagen polymerizes and makes polymeric particles with regularly staggered structure available to induce platelet aggregation. However, this polymeric particle was not precipitated, but was homogeneously dispersed in 0.001 M acetate buffer, pH 5.0. After equilibration the collagen solution was taken from the dialysis bag and UV irradiated in the same manner as in Example 2. The irradiation introduces crosslinkages to stabilize the regularly staggered structure of polymeric collagen. The UV-irradiated polymeric collagen was precipitated at pH 7-8, washed with water twice and lyophilized. The lyophilized collagen was methylated by the method of Example 1. The methylated collagen as dried in a vacuum and redispersed in 5 liters of water. Since methylated collagen contains HCl, the pH of the dispersion gel becomes acidic and the collagen is easily solubilized; however, the regularly staggered quaternary of polymeric collagen is maintained. The pH of the gel was adjusted to 5.0.

The hemostatic agent of the methylated collagen gel prepared by this method was significantly effective for hemostasis and revealed no foreign body reaction and only minimal inflammatory reaction in a dog.

EXAMPLE 8:

The UV-irradiated polymeric collagen was prepared by the method described in Example 7. This collagen was, however, guanidinated by the procedure of Example 3. After guanidination the polymeric collagen was collected by centrifugation and washed with water three times. The collagen was dispersed in 5 liters of water and the pH adjusted to 5.0 by adding HCl to make it gel. The guanidinated collagen dispersed in this gel maintains the regularly staggered polymeric collagen particle large enough to induce platelet aggregation.

The collagen gel prepared by this method was very effective for hemostasis and revealed no foreign body reaction and only minimal inflammatory reaction in a dog.

EXAMPLE 9:

The methylated collagen with stabilized regularly staggered structure of polymeric form was prepared and lyophilized by the method of Example 7. One hundred grams of lyophilized collagen were redispersed in 1 liter of water and the pH adjusted to 9.5 by adding NaOH. The guanidination of this collagen was carried out by the method of Example 3. After guanidination the polymeric collagen was collected by centrifugation and washed with water three times. The collagen was dispersed in 5 liters of water and the pH adjusted to 5.0 by adding HCl to make it gel. The methylated-guanidinated collagen dispersed in this gel maintains the regularly staggered polymeric collagen particle large enough to induce platelet aggregation.

The collagen gel prepared by this method was very effective for hemostasis and revealed no foreign body reaction and only minimal inflammatory reaction in a dog.

In place of methanol in the above reactions other alcohols may be employed, preferably other water-soluble aliphatic alcohols such as ethanol, propanol, etc.

It is essential that the collagen fiber which is modified in accordance with the teaching of this invention be maintained in the proper alignment of structure and configuration as follows: A minimum size molecular mass is necessary for platelet aggregation activity. For example, a single or double molecule of collagen is not active. A minimum tropocollagen molecular length of 7,000 to 10,000 A° is required as well as a minimum diameter of 20–40 A°. The above figures represent 2+ molecular lengths and diameters of collagen. One molecular length is approximately 2,800 Å and one molecular diameter is approximately 15 A°. Furthermore, a periodicity of at least 670–700 A° must be maintained in the collagen fiber. The above dimensions are minimum sizes to induce platelet activity in the collagen, and larger sizes are preferred. This structure and molecular size must be maintained in the collagen fiber during chemical modification. This requirement limits the kind and severity of the modification. Any chemical reaction to induce the desired modification must be relatively mild. Thus, the chemical modification could not tolerate a temperature much above 40° C.

The second feature of the modified polymeric collagen of the present invention is that the collagen molecular structure must display more positive net electrostatic charge preferably by guanidinating the polymer, or subjecting the polymer to esterification, or a combination of the two, i.e., esterification-guanidination, all as explained above.

Having described the invention as above in specific detail, what is claimed is:

1. An improved collagen hemostatic agent comprising enzyme-solubilized telopeptide-poor, crosslinked, polymeric collagen of regularly staggered quaternary structure having a minimum molecular length of 7000 A°, a minimum molecular diameter of 20 A°, a minimum periodicity of 670–700 A° and whose residual lysyl and carboxyl groups have been subjected respectively to at least one reaction selected from the group consisting of guanidination, esterification and guanidination-esterification to greatly enhance the net positive electrostatic charge of the collagen polymer.

2. A hemostatic agent of claim 1 which the polymeric collagen lysyl residues have been guanidinated.

3. A hemostatic agent of claim 1 in which the polymeric collagen carboxyl residues have been esterified.

4. A hemostatic agent of claim 1 in which the polymeric collagen lysyl and carboxyl residues have been guanidinated and esterified respectively.

5. A hemostatic agent of claim 1 in which the polymeric collagen is in gel form.

6. A hemostatic agent of claim 1 in which the polymeric collagen is in powdered form.

7. A process for the preparation of an improved collagen hemostatic agent which comprises extracting collagen from a source of collagen by treatment with a proteolytic enzyme, polymerizing the extract to polymeric collagen of regularly staggered quaternary structure having a minimum molecular length of 7,000 A°, a minimum molecular diameter of 20 A° and a minimum periodicity of 670–700 A°, crosslinking the extracted collagen polymer, and subjecting the crosslinked polymer to at least one reaction selected from the group consisting of esterification, guanidination and guanidination-esterification, whereby the net positive electrostatic charge of the collagen polymer is greatly enhanced.

8. The process according to claim 7 in which the crosslinked, chemically modified polymer is converted to gel form.

9. The process according to claim 7 in which the crosslinked, chemically modified polymer is converted to powdered form.

* * * * *